(12) United States Patent
Cinader et al.

(10) Patent No.: US 7,140,876 B2
(45) Date of Patent: Nov. 28, 2006

(54) ORTHODONTIC APPLIANCE WITH LATCH FOR RETAINING AN ARCHWIRE

(75) Inventors: David K. Cinader, Yorba Linda, CA (US); Jirina V. Pospisil, Hacienda Heights, CA (US); James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 406 days.

(21) Appl. No.: 10/698,285

(22) Filed: Oct. 31, 2003

(65) Prior Publication Data
US 2005/0095549 A1    May 5, 2005

(51) Int. Cl.
*A61C 3/00* (2006.01)
(52) U.S. Cl. ............................. 433/10; 433/8
(58) Field of Classification Search ............... 433/8–17
See application file for complete search history.

(56) References Cited

U.S. PATENT DOCUMENTS

| 1,991,047 | A |   | 2/1935  | Boyd et al. |         |
|-----------|---|---|---------|-------------|---------|
| 3,327,393 | A |   | 6/1967  | Brader      |         |
| 3,724,074 | A |   | 4/1973  | Wallshein   |         |
| 4,103,423 | A |   | 8/1978  | Kessel      |         |
| 4,171,568 | A |   | 10/1979 | Forster     |         |
| 4,248,588 | A | * | 2/1981  | Hanson      | 433/11  |
| 4,355,975 | A |   | 10/1982 | Fujita      |         |
| 4,551,094 | A |   | 11/1985 | Kesling     |         |
| 4,712,999 | A |   | 12/1987 | Rosenberg   |         |
| 5,269,681 | A |   | 12/1993 | Degnan      |         |
| 5,358,402 | A |   | 10/1994 | Reed et al. |         |
| 5,366,372 | A |   | 11/1994 | Hansen et al. |       |
| 5,380,196 | A |   | 1/1995  | Kelly et al. |        |
| 5,439,379 | A |   | 8/1995  | Hansen      |         |
| 5,474,445 | A |   | 12/1995 | Voudouris   |         |
| 5,516,284 | A |   | 5/1996  | Wildman     |         |
| 5,630,715 | A |   | 5/1997  | Voudouris   |         |
| 5,685,711 | A |   | 11/1997 | Hanson      |         |
| 5,711,666 | A |   | 1/1998  | Hanson      |         |
| 5,857,850 | A |   | 1/1999  | Vourdouris  |         |
| 5,863,199 | A |   | 1/1999  | Wildman     |         |
| 6,302,688 | B1 |  | 10/2001 | Jordan et al. |       |
| 6,325,622 | B1 |  | 12/2001 | Kelly et al. |        |
| 6,394,798 | B1 | * | 5/2002 | Huff et al. | 433/8   |
| 6,582,226 | B1 |  | 6/2003  | Jordan et al. |       |
| 2001/0029008 | A1 | | 10/2001 | Jordan et al. |       |
| 2002/0197581 | A1 | | 12/2002 | Georgakis et al. |    |
| 2003/0064342 | A1 | * | 4/2003 | Fukutomi  | 433/8   |

FOREIGN PATENT DOCUMENTS

WO    WO 98/20805    5/1998

OTHER PUBLICATIONS

Pending U.S. Appl. No. 10/287,089, filed Nov. 4, 2002.
Pending U.S. Appl. No. 10/287,165, filed Nov. 4, 2002.
Pending U.S. Appl. No. 10/730,344, filed Dec. 8, 2003.

* cited by examiner

*Primary Examiner*—Cris L Rodriguez
*Assistant Examiner*—Candice C. Stokes
(74) *Attorney, Agent, or Firm*—James D. Christoff (57) ABSTRACT

An orthodontic appliance includes a latch that comprises at least one clip with a region for receiving an archwire. The clip also includes a recess for receiving a post of the appliance, and the recess is not in communication with the archwire-receiving region. The post functions to secure the clip to remaining components of the appliance, such as a body or base of the appliance. Optionally, the clip may include a second recess for receiving a second post of the appliance.

33 Claims, 6 Drawing Sheets

ORTHODONTIC APPLIANCE WITH LATCH FOR RETAINING AN ARCHWIRE

BACKGROUND OF THE INVENTION

1. Field of the Invention

This invention broadly relates to appliances that are used during the course of orthodontic treatment. More particularly, the present invention relates to an orthodontic appliance such as a bracket or molar appliance having a latch that releasably retains an archwire in an archwire slot.

2. Description of the Related Art

Orthodontic therapy is a specialized type of treatment within the field of dentistry, and involves movement of malpositioned teeth to orthodontically correct locations. Orthodontic treatment typically enhances the aesthetic appearance of the teeth, particularly in instances when the patient's front teeth are malpositioned or crooked. Orthodontic treatment can also improve the patient's occlusion so that the teeth interact better with each other during mastication.

Many type of orthodontic treatment programs involve the use of a set of tiny appliances and wires that are commonly known collectively as "braces". During such treatment programs, small slotted appliances known as brackets are fixed to the patient's anterior, cuspid and bicuspid teeth, and an archwire is inserted into the slot of each bracket. The archwire forms a track to guide movement of the teeth to orthodontically correct locations. End sections of the archwires are typically captured in tiny appliances known as buccal tubes that are fixed to the patient's molar teeth.

Orthodontic brackets often have archwire slots that are open on one side for insertion of the archwire and that are bounded on remaining sides by walls or other structure of the brackets. Brackets that are affixed to the patient's buccolabial tooth surfaces (i.e., the surfaces of the teeth facing the patient's cheeks or lips) often have archwire slots that are open on a buccolabial side of the archwire slot. Brackets that are fixed to the lingual surfaces of the patient's teeth (i.e., the surfaces of the teeth facing the patient's tongue) often have an archwire slot that is open either on a lingual side or on an occlusal side (i.e., a side of the slot facing the outer tips of the teeth).

In the past, orthodontic practitioners commonly used elastomeric ligatures or wire ligatures to connect the archwire to the brackets and to urge the archwire into an orientation of seated engagement with the bottom of the archwire slot. Ligatures are typically installed by extending the ligature about the archwire as well as behind tiny protruding hooks known as "tiewings" that extend outwardly from a body of the bracket.

Recently, there has been increased interest in orthodontic appliances that have a latch for coupling the archwire to the appliance. Appliances of this type are widely known as self-ligating appliances and often obviate the need to use ligatures. A number of different latches are known, including movable clips, spring members, covers, shutters, bales and other structure. The latches are connected to a body of the appliance for releasably retaining the archwire in the archwire slot.

Improved self-ligating orthodontic appliances are described in two U.S. patents entitled "ORTHODONTIC APPLIANCE WITH SELF-RELEASING LATCH", U.S. Pat. Nos. 6,302,688 and 6,582,226. The appliances described in those patents have a latch for retaining an archwire in the archwire slot, and the latch releases the archwire from the archwire slot whenever the archwire exerts a force on the appliance that exceeds a certain minimum value. The minimum value is significantly less than the force required in the same direction to debond the appliance from the tooth, and consequently helps to ensure that the appliance will not spontaneously debond from the tooth during the course of treatment.

In certain embodiments of the appliances described in the two U.S. patents mentioned above, the archwire may be inserted into the archwire slot by pressing the archwire against the latch. The latch is constructed to self-open without the need for hand instruments or other tools. Consequently, such appliances are a great advantage to the practitioner in that the time needed for connecting the archwire to the appliance can be significantly reduced.

In some of the appliances described in U.S. Pat. Nos. 6,302,688 and 6,582,226, the latch of the appliance comprises one or two resilient clips having a generally U-shaped configuration, and the clips spread open to admit an archwire into the archwire slot of the appliance. Preferably, the clips are made of a shape-memory alloy such as alloys of nitinol and beta-titanium in order to help assure that the clip reliably opens and closes as intended over extended periods of time. The use of shape-memory alloys also helps to ensure that the clip does not fracture during use so that the appliance need not be replaced once it is bonded to the patient's tooth.

However, clips that are made of nitinol and beta-titanium can present problems for the manufacturer during assembly of the appliance. For example, the resilient properties of such clips may be adversely affected if the clip is exposed to undue heat during assembly of the appliance, such as heat from a brazing or welding process. Brazing and welding processes are often used to join a base of the appliance, such as a mesh-type base, to a body of the appliance that has been separately manufactured.

Moreover, it is desirable to avoid increasing the overall size of the appliance when attempting to alter or improve the connection between the clip and remaining components of the appliance. An increase in the size of the appliance may increase the likelihood that the appliance will impinge on adjacent soft tissue in the oral cavity and cause discomfort to the patient. In addition, an increase in appliance size will often cause the appliance to be more visible to casual observers and adversely affect its aesthetic appearance.

Accordingly, it would be advantageous to provide a new self-ligating orthodontic appliance having improved means for connecting a clip of the appliance to remaining components of the appliance.

SUMMARY OF THE INVENTION

The present invention is directed toward a self-ligating orthodontic appliance having an improved construction for assembling and coupling a latch to remaining components of the appliance. The latch includes a clip having a recess, and the recess surrounds a post of the appliance that is provided to retain the clip in place. Preferably, a section of the clip adjacent the recess is resilient and movable in order to admit the post into the recess when the appliance is assembled.

In more detail, the present invention is directed to an orthodontic appliance that comprises a base and a body extending outwardly from the base. An archwire slot extends across the appliance in a generally mesial-distal direction. The appliance also includes a post and a latch for releasably retaining an archwire in the archwire slot. The latch includes a clip having a region next to the archwire slot for receiving the archwire. The clip also includes a recess that receives the post, and the recess is not in communication with the archwire-receiving region.

The present invention is an advantage, in that the clip can be assembled to remaining components of the appliance after the completion of any process steps carried out at elevated temperatures. For example, the clip can be assembled to remaining components of the appliance after the base of the appliance has been welded or brazed to the appliance body. As a consequence, the resilient properties of the clip are not impaired by heat from the welding or brazing operation.

Optionally, the clip may include more than one recess, each of which receives a respective post. For example, the clip may include two recesses that are located on opposite sides of the archwire-receiving region, and each of the recesses are not in communication with the archwire-receiving region.

The latch may include only a single clip, or alternatively comprise two or more clips. If only a single clip is provided, it may be located near the center of the archwire slot along its length. If two clips are provided, the clips may be located near mesial and distal ends of the archwire slot and optionally next to mesial and distal sides of the appliance body.

Additional aspects and features of the invention are set out in the detailed description that follows and are illustrated in the accompanying drawings.

DETAILED DESCRIPTION OF THE PREFERRED EMBODIMENTS

An orthodontic appliance constructed in accordance with one embodiment of the present invention is illustrated in FIGS. 1–4 and is broadly designated by the numeral 20. The appliance 20 in this instance is an orthodontic bracket that is adapted to be secured to an enamel surface of a patient's tooth, such as a buccolabial surface. Alternatively, the appliance could be a molar appliance or any other orthodontic appliance that is adapted to receive an archwire for controlling movement of the teeth during the course of orthodontic therapy.

Figure 1:
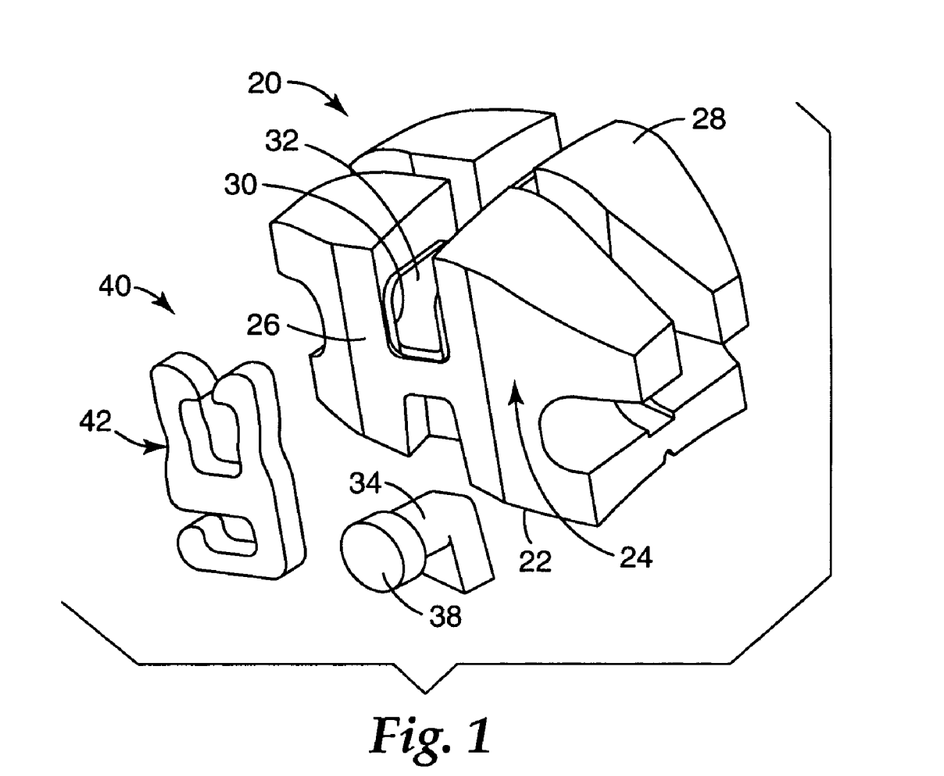
FIG. 1 is an exploded perspective view of an orthodontic appliance constructed in accordance with one embodiment of the present invention, looking at the appliance toward its mesial, buccolabial and gingival sides.
Figure 2:
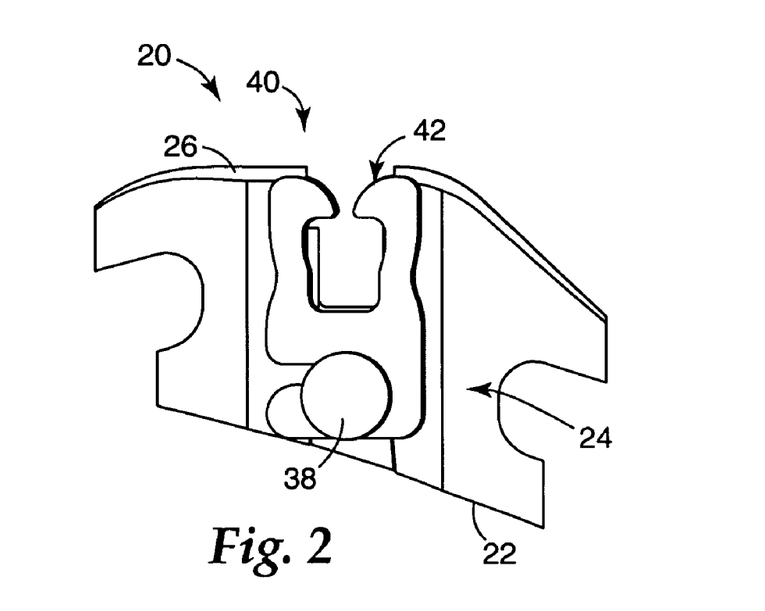
FIG. 2 is an assembled view of the appliance depicted in FIG. 1, looking at the appliance toward its mesial side.
Figure 3:
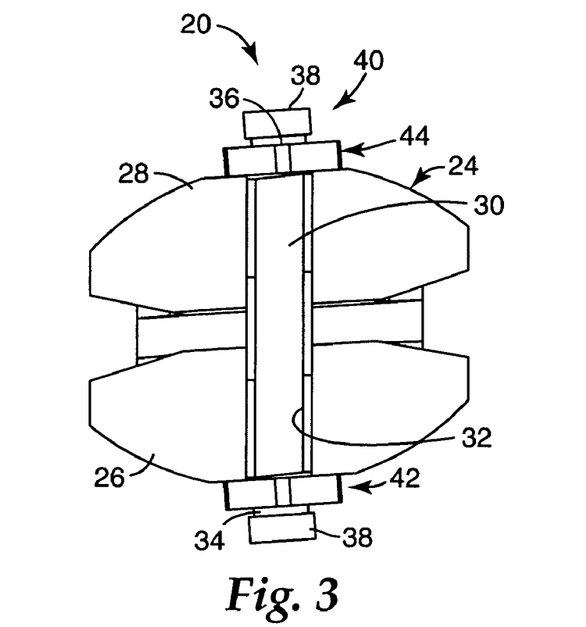
FIG. 3 is an assembled view of the appliance shown in FIGS. 1 and 2, looking at the appliance toward its labial side.

The appliance 20 includes a base 22 for bonding the appliance 20 directly to the patient's tooth enamel by the use of an adhesive. Preferably, the base 22 has an outwardly-facing concave compound contour that matches the convex compound contour of the patient's tooth surface to which it is bonded. Optionally, the base 22 is provided with grooves, particles, recesses, undercuts, a chemical bond enhancement material or any other material or structure or any combination of the foregoing that facilitates bonding the appliance 20 directly to the patient's tooth surface.

A body 24 extends outwardly from the base 22 in a generally buccolabial direction. The body 24 includes a mesial body portion 26 and a distal body portion 28 that is spaced from the mesial body portion 26. In this embodiment, each of the portions 26, 28 is integrally connected to an occlusal tiewing and a gingival tiewing, although one or more of the tiewings could be omitted if desired.

Preferably, and as shown in FIGS. 1–3, the body 24 including the portions 26, 28 are integrally connected to the base 22 and form a single, unitary element. However, other constructions are also possible. For example, if the base and the body are made of metallic materials, the base could be manufactured separately from the body and later welded or brazed to the body during an assembly operation.

The appliance 20 also includes an optional archwire slot liner 30 that is fixed to the body portions 26, 28. The archwire slot liner 30 defines occlusal, gingival and lingual (bottom) sides of an archwire slot 32. The archwire slot 32 longitudinally extends in a mesial-distal direction across the appliance 20, including through a channel of the body portions 26, 28.

The base 22, the body 24 and the archwire slot liner 30 are preferably similar to the corresponding components of the appliances described in U.S. Pat. Nos. 5,439,379 and 5,366,372, both of which are expressly incorporated by reference herein. Preferably, the base 22 and the body 24 are made of a translucent polycrystalline ceramic material such as alumina, while the archwire slot liner 30 is made of a metallic material. Examples of suitable materials and methods for constructing the archwire slot liner 30, as well as examples of suitable methods for attaching the archwire slot liner 30 to the body portions 26, 28 are described in U.S. Pat. Nos.

5,358,402 and 5,380,196, both of which are also expressly incorporated by reference herein.

The appliance 20 includes a mesial post 34 and a distal post 36 that are connected to the mesial body portion 26 and the distal body portion 28 respectively. The posts 34, 36 extend outwardly in opposite directions away from each other and from the body 24, preferably in directions perpendicular to adjacent regions of the mesial side of the body portion 26 and the distal side of the body portion 28. In instances where the bracket is non-angulated or has a relatively small angulation, the posts 34, 36 also extend in generally parallel relationship to the longitudinal axis of the archwire slot 32. Each of the posts 34, 36 includes an outermost enlarged head 38 having a cylindrical shape, although other shapes are also possible.

In the illustrated embodiment, the posts 34, 36 are made of a metallic material and have an end portion that fits into mating holes provided in the corresponding body portions 26, 28. Optionally, the end portion has a trapezoidal shape that is nearly a rectangle, in order to facilitate the establishment of a tight, mating fit between the post 34 and the body 24.

Preferably, the posts 34, 36 are secured to the body portions 26, 28 by a welding or brazing process. Suitable brazing processes are described in U.S. Pat. Nos. 5,358,402 and 5,380,196. However, other constructions are possible. For example, the posts 34, 36 could be integrally connected to the body portions 26, 28, as may be desired in instances when the body 24 and the posts 34, 36 are made of a metallic material. As an additional option, the body 24 and the posts 34, 36 can be initially manufactured as discrete, separate components made of a metallic material that are subsequently connected together by a welding or brazing process.

The appliance 20 also includes a latch 40 for releasably retaining an archwire (not shown) in the archwire slot 32. In the exemplary embodiment shown in FIGS. 1–3, the latch 40 includes a mesial clip 42 and a distal clip 44, although other constructions are also possible. For instance, the latch could comprise a single clip that is located in the space between the mesial and distal body portions 26, 28, or could alternatively include three or more clips that are spaced along the length of the archwire slot.

Figure 4:
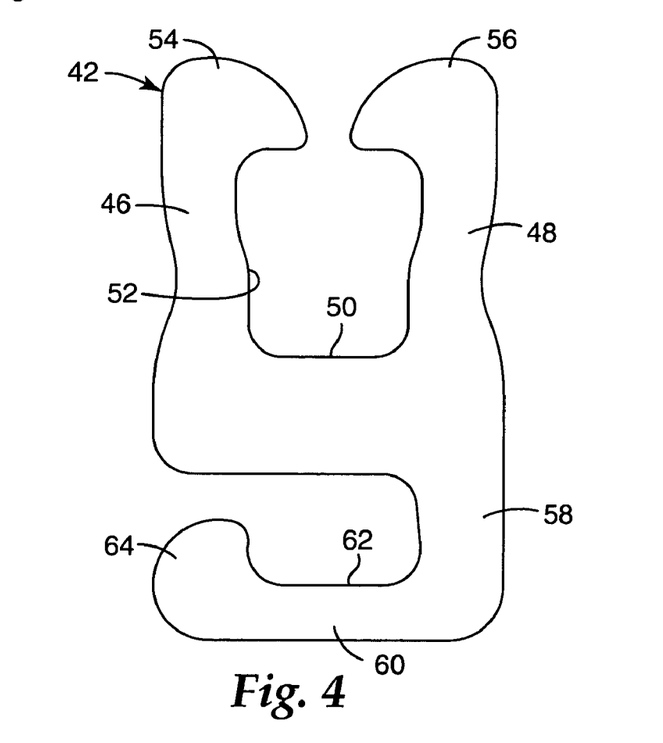
FIG. 4 is an enlarged side elevational view of a clip of the appliance illustrated in FIGS. 1–3.

The mesial clip 42 is shown alone in enlarged view in FIG. 4. The clip 42 includes a first elongated section 46 and a second elongated section 48 that is opposed to the first section 46. In their normal, relaxed configurations, the first section 46 and the second section 48 extend in generally parallel directions. A third section 50 interconnects the first and second sections 46, 48 and extends in a direction generally perpendicular to the same.

The sections 46, 48, 50 together present a generally "U"-shaped configuration and define a region 52 for receiving an archwire. When the clip 42 is assembled to the body portion 26, the sections 46, 48 extend in directions generally along a buccolabial-lingual reference axis, and the third section 50 extends in directions generally along an occlusal-gingival reference axis.

The clip 42 also includes two arm portions 54, 56 that extend inwardly toward each other. A buccolabial edge of each arm portion 54, 56 is smoothly curved in an arc about a mesial-distal reference axis. The arm portion 54 is connected to an outer end of the first clip section 46, while the arm portion 56 is connected to an outer end of the second clip section 48.

The clip 42 is shown in its normal, relaxed orientation in the drawings. However, the arm portions 54, 56 are movable away from each other in order to admit an archwire into the archwire-receiving region 52 when desired. To this end, the first and second sections 46, 48 deflect outwardly when the clip 42 is opened and bend in respective arcs away from each other in order to enable the arm portions 54, 56 to move apart from each other.

The smooth, outer edge of the arm portions 54, 56 enables the clip 42 to open and admit an archwire into the region 52 by pressing an archwire against the outer curved edges of the arm portions 54, 56. As pressure is exerted by the archwire on the curved edges, the first and second sections 46, 48 deflect away from each other in order to admit the archwire into the region 52. Once the archwire is received in the region 52, the inherent resiliency of the clip 42, and particularly the resiliency of the first and second sections 46, 48, enables the arm portions 54, 56 to spring back toward each other and toward their normal, relaxed configurations as shown in FIGS. 1–4 in order to retain the archwire in the archwire slot 32.

The clip 42 also includes a fourth section 58 that is connected to the third section 50. The fourth section 58 extends away from the third section 50 in a direction generally parallel to the longitudinal axis of the second section 48. Optionally, and as shown in the drawings, the fourth section 58 is in general alignment with the second section 48.

The clip 42 further includes a leg section 60 that is connected to the fourth section 58. The leg section 60 extends in a direction generally parallel to the third section 50. The third section 50, the fourth section 58 and the leg section 60 together present a generally "U"-shaped configuration and define a recess 62 having a gingival opening for receiving the mesial post 34.

The recess 62 is not in communication with the archwire-receiving region 52. This means that the clip 42 has structure that prevents the post 34 from moving from the recess 62 and into the region 52. Preferably, the structure is a solid section of the clip 42. In the illustrated embodiment, the third section 50 prevents the post 34 from moving from the recess 62 into the region 52 and provides a means for prohibiting communication between the recess 62 and the region 52. The opening or entrance to the recess 62 is oriented at an angle that is approximately 90 degrees relative to the opening to the region 52.

An outer portion of the leg section 60 is connected to an end section 64. An outer-most, gingival edge of the end section 64 is smoothly curved in an arc that extends about a mesial-distal reference axis.

The leg section 60 is resilient and movable away from the third section 50 in order to admit the post 34 into the recess 62. Optionally, the fourth section 58 is also resilient. During manufacture of the appliance 20, the clip 42 is urged in an occlusal direction (or alternatively or in addition the body 24 is moved in a gingival direction) such that the post 34 comes into contact with the portion of the outer curved edge of the end section 64 that is nearest the third section 50. As continued pressure is exerted on the clip 42, the leg section 60 deflects outwardly and away from the third section 50 and enables the post 34 to be received in the recess 62.

Once the post 34 is located in the recess 62, the inherent resiliency of the leg section 60 and optionally of the fourth section 58 enables the same to move back to their normal, relaxed orientations as shown in the drawings. Thereafter, the end section 64 retains the clip 42 in place adjacent the mesial side of the mesial body portion 26. Preferably, the leg section 60 and the fourth section 58 are sufficiently stiff to substantially preclude unintentional deflection of the leg section 60 in order to help ensure that the clip 42 remains assembled to the body portion 26 during the entire course of orthodontic treatment.

Preferably, the post 34 includes one or more flat sides that are in mating contact with one or more respective flat regions of the clip 42. For example, and in the embodiment shown in FIGS. 1–3, the post 34 includes a flat buccolabial side and a flat lingual side that engage flat regions of the third section 50 and the leg section 60 respectively. Such flat areas of contact between the post 34 and the clip 42 help ensure that the clip 42 does not unduly shift or rock during use, such as rocking movement in an arc about the central axis of the post 34. Preferably, however, the occlusal side of the post 34 is rounded in order to facilitate outward deflection of the leg section 60 when the clip 42 is assembled to the body portion 26.

The clip 42 (including the first and second sections 46, 48) is sufficiently stiff to retain the archwire in the archwire slot 32 during the course of treatment so long as the forces exerted by the archwire on the appliance 20 are below a certain minimum value in a generally buccolabial direction (more particularly, in a direction opposite to the direction of insertion of the archwire into the archwire slot 32). However, whenever the forces exerted by the archwire on the appliance 20 in the same direction are greater than the minimum value, as might occur when unexpectedly high forces are encountered, the first and second sections 46, 48 deflect outwardly and the arm portions 54, 56 move apart from each other to open the clip 42 and enable the archwire to be released from the archwire slot 32. Further details regarding such forces are described in the aforementioned U.S. Pat. Nos. 6,302,688 and 6,582,226, both of which are expressly incorporated by reference herein.

Preferably, the clip 42 is identical to the clip 44. The latch 40, comprising the clips 42, 44, preferably releases the archwire from the archwire slot 32 in a generally buccolabial direction whenever the archwire exerts a force in the same direction on the appliance 20 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 32 during the normal course of orthodontic treatment. As such, the archwire can exert forces on the appliance 20 sufficient to carry out the treatment program and move the associated teeth as desired.

Preferably, the minimum value for self-release (i.e., self-opening) of the latch 40 is substantially less than the force required in the same direction to debond the appliance 20 from the associated tooth. The minimum value for self-release of the latch 40 is preferably less than about one-half of the force required in the same direction to debond the appliance 20 from the associated tooth. For example, if the expected bond strength of the adhesive bond between the appliance 20 and the associated tooth is 16 lbs (7.2 kg) in a buccolabial direction, the latch 40 is constructed to self-release the archwire whenever the archwire exerts a force in the same buccolabial direction on the appliance 20 that is somewhat greater than about 8 lbs (3.6 kg).

To determine the force to release the latch 40, a section of archwire is selected having an area in longitudinally transverse sections that is complemental to (i.e., substantially fills) the cross-sectional area of the archwire slot 32. Next, a sling is constructed and is connected to the archwire section at locations closely adjacent, but not in contact with the heads of the posts 34, 36 including the head 38. Optionally, the sling is welded or brazed to the archwire section. Next, the sling is pulled away from the appliance 20 while the appliance 20 is held in a stationary position, taking care to ensure that the longitudinal axis of the archwire section does not tip relative to the longitudinal axis of the archwire slot 32. The force to release the latch 40 may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y.) to measure the force.

Preferably, the distance between the opposed ends of the arm portions 54, 56 is less than the overall occlusal-gingival dimension of the smallest archwire expected to be used during the course of treatment. The archwire need not fill the archwire slot 32 and flatly engage the wall portions defining the archwire slot 32 in all instances. For example, a somewhat smaller wire, and perhaps an archwire having a circular cross-sectional shape, may be used during a portion of the treatment program. The distance between the opposed ends of the arm portions 54, 56 is preferably selected so that a variety of archwires of different cross-sectional configurations may be used in connection with the appliance 20.

Preferably, the distal clip 44 is identical to the mesial clip 42. Optionally, however, it is possible to construct the clips 42, 44 somewhat differently to address certain circumstances. For example, if a malpositioned tooth is initially oriented such that its mesial side is rotated in a lingual direction, it may be desirable to increase the stiffness of the mesial clip 42 so that a somewhat greater force is needed to release the archwire from the archwire slot 32 in comparison to the force needed to release the archwire from the distal clip 44. Other options are also possible.

Optionally, the spring clips 42, 44 are cut from a flat section of metallic stock material. Suitable metallic materials include shape memory alloys such as alloys of nitinol and beta-titanium. The clips 42, 44 may be cut from the stock material using a stamping, die cutting, chemical etching, EDM (electrical discharge machining), laser cutting or water jet cutting process. As another option, the clips 42, 44 could be formed and then heat treated to set their shapes.

As presently preferred, the clips 42, 44 are made from flat annealed superelastic material (such as nitinol) having a pickled surface. Preferred nitinol materials have a nickel content of 55.97% by weight $A_f$ of 10°±5° C. The nitinol is cold worked to 37.5% and has a thickness in the range of about 0.012 in. (0.3 mm) to about 0.016 in. (0.4 mm). The clips 42, 44 are first cut in a rough cutting EDM process, then cut along their edges for an additional one or more times using an EDM process in order to smooth the edges. Alternatively, a laser cutting process or chemical etching process could be used to make the clips 42, 44. Preferably, the clips 42, 44 are constructed so that the longitudinal direction of the clip material, or the principal direction of grain flow of the clip material, is substantially parallel to the direction of extension of the first and second sections 46, 48 (i.e. a generally buccolabial direction ).

Subsequent to the EDM, laser cutting or chemical etching process, the clips 42, 44 are tumbled in order to further round their edges. An example of a suitable tumbling machine is model LC-600-2+2 from Richwood Industries. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size $3/16 \times 3/8$ (4.7 mm×9.5 mm)), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. TI121 Pickling Solution from Aya International of Los Angeles, Calif.

Other optional aspects of the clips 42, 44 are described in pending U.S. patent application entitled "ORTHODONTIC APPLIANCE WITH FATIGUE-RESISTANT ARCHWIRE RETAINING LATCH"; Ser. No. 10/287,089 filed Nov. 4, 2002, which is also hereby incorporated by reference herein.

Figure 5:
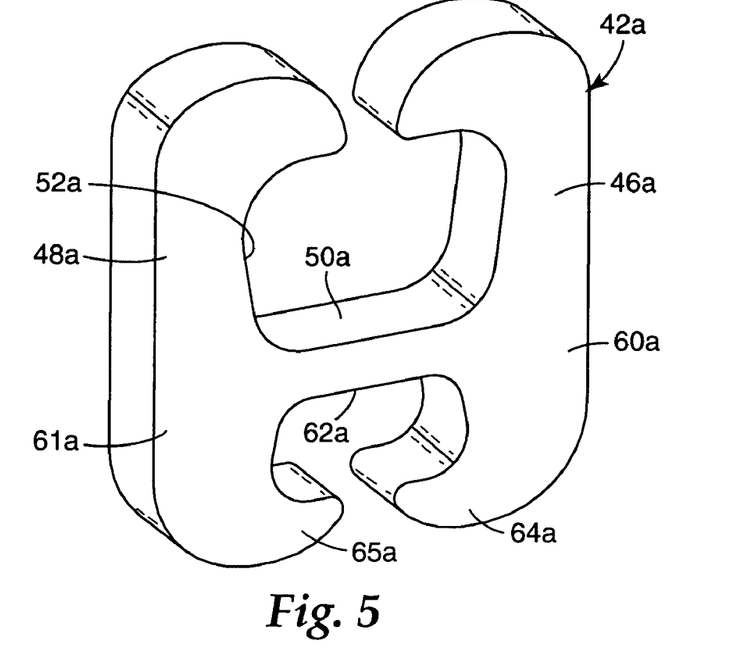
FIG. 5 is an enlarged perspective view of a clip of an appliance according to another embodiment of the invention.

Another embodiment of the invention is illustrated in FIG. 5, wherein a clip 42a is shown in perspective view. The clip 42a is part of an appliance that is not depicted in the drawings. However, the appliance (except for the clips such as clip 42a) may be otherwise similar to or identical to the appliance 20 shown in FIGS. 1–3.

The clip 42a has a first section 46a, a second section 48a and a third section 50a. The sections 46a, 48a, 50a are preferably similar to the sections 46, 48, 50 respectively described above and together partially define an archwire-receiving region 52a.

The clip 42a also includes a first leg section 60a and a second leg section 61a. The leg section 60a extends in a direction generally parallel to the direction of extension of the first section 46a, and the leg section 61a extends in a direction generally parallel to the direction of extension of the second section 48a. The sections 60a, 61a are integrally connected to opposite ends of the third section 50a.

The third section 50a, the leg section 60a and the leg section 61a together define a recess 62a with a lingual opening for receiving a post, such as the mesial post 34 described above. The recess 62a is not in communication with the archwire-receiving region 52a. The third section 50a prevents the post from moving between the recess 62a and the region 52a. The opening or entrance to the recess 62a is oriented at an angle of approximately 180 degrees relative to the opening to the archwire-receiving region 52a.

An outer portion of the leg section 60a is connected to an end section 64a. An outer portion of the leg section 61a is connected to an end section 65a. An outermost, lingual edge of the end sections 64a, 65a is preferably smoothly curved in an arc that extends about a mesial-distal reference axis.

Preferably, at least one of the leg sections 60a, 61a, and preferably both of the leg sections 60a, 61a, are resilient and movable away from each other in order to admit a post into the recess 62a. During assembly of the appliance, the clip 42a is urged in a lingual direction (or alternatively or in addition the appliance body is moved in a buccolabial direction) such that the post comes into contact with portions of the outermost, curved edges of the end sections 64a, 65a that are near the opening to the recess 62a. As continued pressure is exerted on the clip 42a, one or both of the leg sections 60a, 61a deflect outwardly (i.e., away from the other section) so that the post can be received in the recess 62a.

Once the post is located in the recess 62a, the inherent resiliency of the leg sections 60a, 61a tends to shift the same back to their normal, relaxed orientations as shown in FIG. 5. Thereafter, the end sections 64a, 65a retain the clip 42a in place. Preferably, the leg sections 60a, 61a are sufficiently stiff to substantially preclude unintentional deflection of the sections 60a, 61a in order to help ensure that the clip 42a remains assembled to remaining components of the appliance during the entire course of orthodontic treatment.

Other aspects of the clip are similar to the clip 42 described above. Consequently, a detailed description of the common aspects need not be repeated.

An orthodontic appliance 20b according to another embodiment of the invention is illustrated in FIGS. 6–10. Except as described below, the appliance 20b is essentially identical to the appliance 20 shown in FIGS. 1–4.

The appliance 20b includes a first mesial post 34b along with a second mesial post 35b. The appliance 20b also includes a first distal post 36b and a second distal post 37b. The posts 34b–37b extend in parallel directions, preferably in directions generally perpendicular to adjacent sides of the mesial and distal portions of the appliance body. In instances where the appliance 20b is non-angulated or has only a relatively small angulation, the posts 34b–37b also extend in directions generally parallel to the longitudinal axis of an archwire slot 32b. Each of the posts 34b–37b includes an enlarged head.

A latch 40b of the appliance 20b comprises a mesial clip 42b and a distal clip 44b. The mesial clip 42b is shown alone in FIG. 10. The mesial clip 42b includes a first section 46b, a second section 48b and a third section 50b. Except as described below, the sections 46b, 48b, 50b are essentially identical to the sections 46, 48, 50 respectively described above and together partially define an archwire-receiving region 52b.

Figure 10:
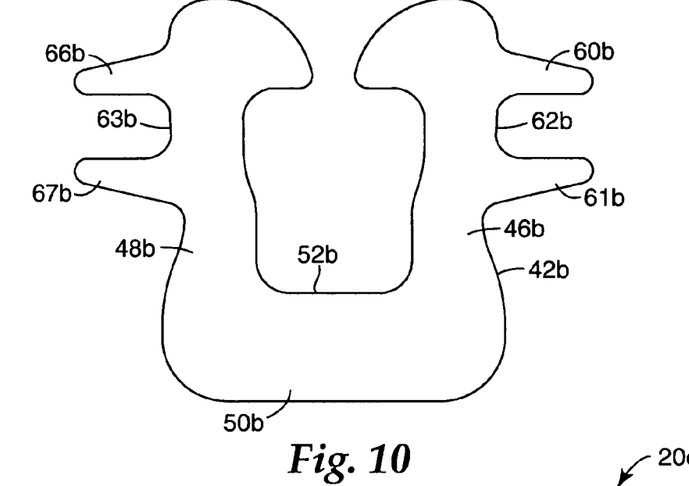
FIG. 10 is an enlarged side elevational view of a clip of the appliance shown in FIGS. 6–9.

The clip 42b also includes a pair of gingival leg sections 60b, 61b and a pair of occlusal leg sections 66b, 67b. The gingival leg sections 60b, 61b are integrally connected to a gingival side of the first section 46b. The occlusal leg sections 66b, 67b are integrally connected to an occlusal side of the second section 48b. As shown, the gingival leg sections 60b, 61b extend in a gingival direction away from the first section 46b, while the occlusal leg sections 66b, 67b extend in an occlusal direction away from the second section 48b.

The leg sections 60b, 61b, along with an adjacent gingival edge portion of the first section 46b, together define a generally "U"-shaped recess 62b for receiving the first mesial post 34b. Similarly, the occlusal leg sections 66b, 67b, together with a occlusal edge portion of the second section 48b, define a generally "U"-shaped recess 63b for receiving the second mesial post 35b. The recesses 62b, 63b are not in communication with the archwire-receiving region 52b, and the sections 46b, 48b preclude the posts 34b, 35b respectively from moving into the region 52b. The openings to the recesses 62b, 63b are opposed to each other and oriented at respective angles that are approximately 90 degrees relative to the opening to the region 52b.

The clip 42b is shown in its normal, relaxed orientation in FIGS. 6–10. As illustrated, a space is present between the posts 34b, 35b and the adjacent edge portion of the first and second sections 46b, 48b when the clip 42b is in its relaxed orientation. The space enables the sections 46b, 48b to deflect and move away from each other when desired in order to admit an archwire into the archwire-receiving region 52b.

Figure 9:
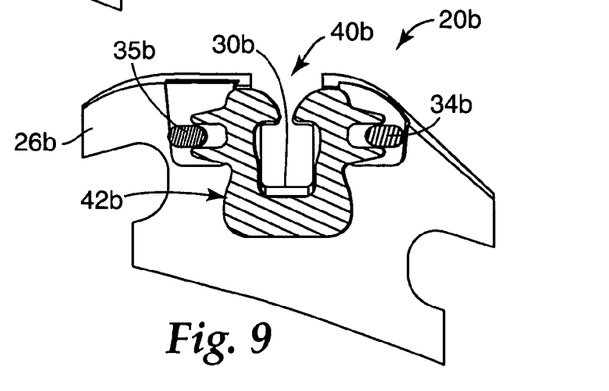
FIG. 9 is a view taken along lines 9—9 of FIG. 7 and is somewhat similar to FIG. 8 except that the appliance is illustrated in partial cross-section.

Preferably, and as shown in FIG. 9, the cross-sectional configuration of the posts 34b, 35b is somewhat flattened in order to reduce the overall buccolabial-lingual dimension of the same. Preferably, the posts 34b, 35b have an inner rectangular end portion that fits into a mating cavity provided in the body of the appliance 20b, in a manner similar to the connection between the post 34 and the body portion 26 as set out in detail above. The posts 34b, 35b have an enlarged head that resembles a trapezoid with rounded ends, although other shapes are also possible.

Figure 6:
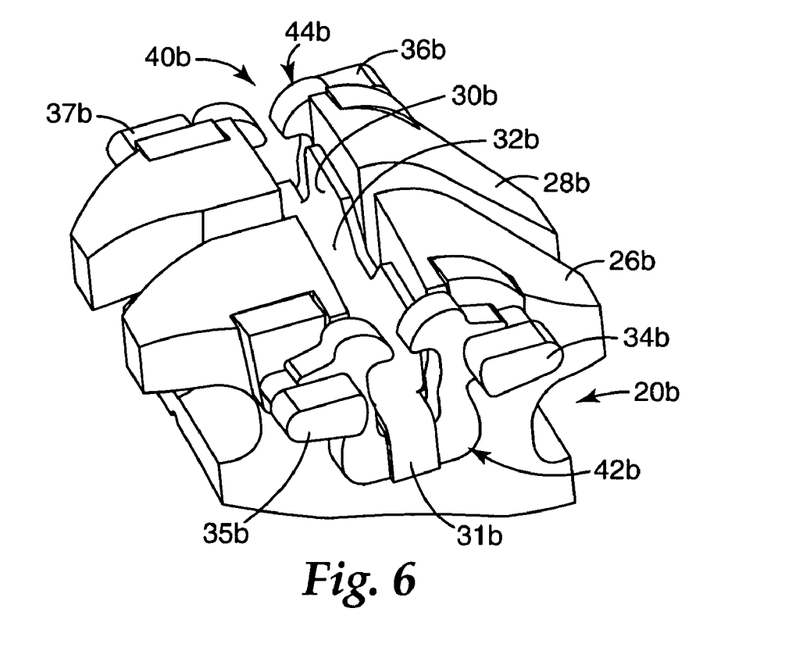
FIG. 6 is a perspective view of an orthodontic appliance according to another embodiment of the present invention, looking at the appliance toward its mesial, buccolabial and occlusal sides.
Figure 7:
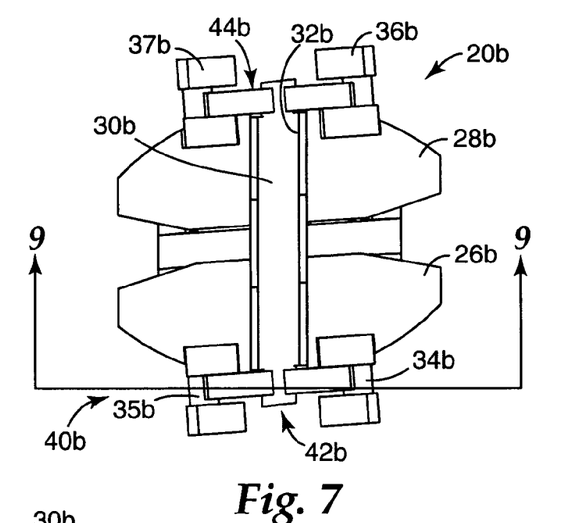
FIG. 7 is a front elevational view of the appliance depicted in FIG. 6, looking at the appliance toward its buccolabial side.
Figure 8:
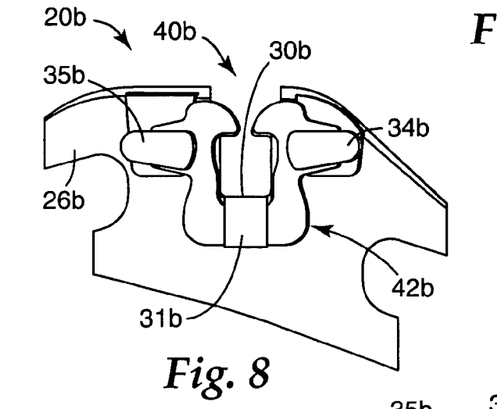
FIG. 8 is a side elevational view of the appliance shown in FIGS. 6–7, looking at the appliance toward its mesial side.

The appliance 20b also has an archwire slot liner 30b that is somewhat similar to the archwire slot liner 30 described above, except that mesial and distal ends of the archwire slot liner 30b extend past mesial and distal body portions 26b, 28b respectively of the appliance 20b. The mesial end portion extends in a lingual direction over the third section 50b of the mesial clip 42b, and the distal end section extends in a lingual direction over the third section of the distal clip 44b. In FIGS. 6 and 8, the mesial end portion of the archwire slot liner 30b is designated by the numeral 31b.

During assembly of the appliance 20b, the sections 46b, 48b are deflected inwardly toward each other a distance sufficient to ensure that the distance between the outer tips of the leg sections 60b, 66b is less than the distance between the facing sides of the posts 34b, 35b. The clip 42b is then moved in a buccolabial direction relative to the appliance body 24b (or, alternatively, the body 24b is moved in a lingual direction relative to the clip 42b) until such time as the post 34b is located between the leg sections 60b, 61b and the post 35b is located between the leg sections 66b, 67b. Subsequently, the force directed inwardly on the first and second sections 46b, 48b is released and the sections 46b, 48b resume their normal, relaxed orientation as depicted in the drawings. The end portion 31b of the archwire slot liner 30b is then bent from its initially straight configuration (i.e., parallel to the longitudinal axis of the archwire slot) and in a lingual direction such that it extends over the third section 50b of the mesial clip 42b. The clip 42b is thereafter retained in place by the leg sections 60b, 61b, 66b, 67b in cooperation with the posts 34b, 35b, as well as by the end portion 31b. The clip 44b is installed in a similar manner.

Figure 11:
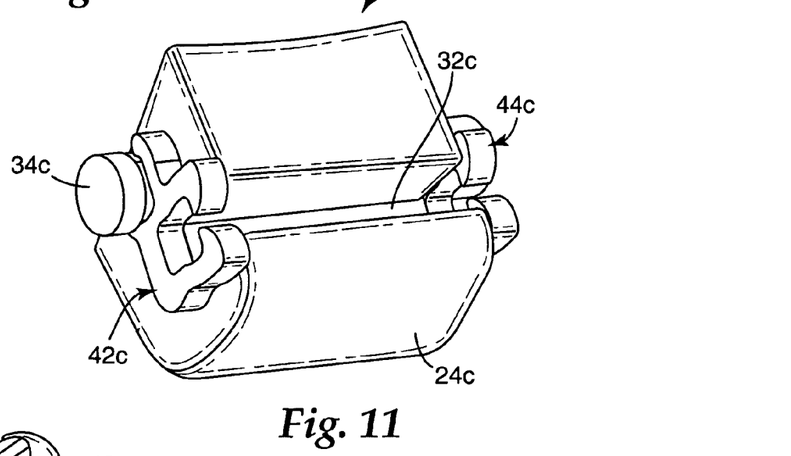
FIG. 11 is a perspective view of an orthodontic appliance according to another embodiment of the invention, looking at the appliance in a direction toward its mesial, occlusal and lingual sides.
Figure 12:
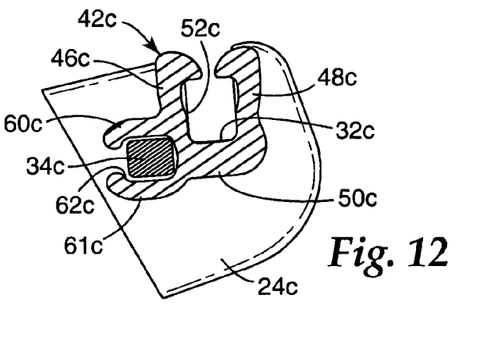
FIG. 12 is a side cross-sectional view of the orthodontic appliance shown in FIG. 11, looking at the appliance in a direction along a mesial-distal reference axis.

An orthodontic appliance 20c according to another embodiment of the invention is illustrated in FIGS. 11 and 12. Except as described below, the appliance 20c is similar to the appliances 20, 20b set out above.

The appliance 20c includes a body 24c along with an archwire slot 32c. A latch of the appliance 20c comprises a mesial clip 42c and a distal clip 44c. The mesial clip 42c is coupled to the body 24c by a mesial post 34c, and a similar post connects the distal clip 44c to the body 24c.

The clip 42c includes a first section 46c, a second section 48c and a third section 50c as shown in FIG. 12. The sections 46c, 48c, 50c together define a region 52c for receiving an archwire.

The mesial clip 42c also includes a first leg section 60c and a second leg section 61c. The first and second leg sections 60c, 61c extend in a direction generally parallel to the direction of extension of the third section 50c. The leg section 60c is integrally connected directly to the first section 46c, and the leg section 61c is integrally connected directly to a region of the clip 42c that is adjacent the intersection of the first section 46c and the third section 50c.

The leg sections 60c, 61c, along with an adjacent portion of the first leg section 46c, together define a recess 62c for receiving the mesial post 34c. The recess 62c is not in communication with the archwire-receiving region 52c. The first section 46c prevents the post 34c from moving between the recess 62c and the region 52c. In this embodiment, the opening to the recess 62c is oriented at an angle of approximately 90 degrees relative to the opening of the archwire-receiving region 52c.

Preferably, and as illustrated in FIG. 12, the cross-sectional configuration of the post 34c includes flat sides that flatly engage straight inner edges of the first and second leg sections 60c, 61c. Such areas of flat, mating contact help ensure that the clip 42c does not unduly pivot in an arc in directions about the central axis of the post 34c (which preferably is parallel to or at least generally parallel to the longitudinal axis of the archwire slot 32c). As a result, the archwire-receiving region 52c remains in substantial alignment with the archwire slot 32c.

The appliance 20c as depicted in FIGS. 11 and 12 is especially adapted for use on a lingual surface of a patient's tooth, and in this exemplary embodiment tiewings for receiving a ligature are not provided. However, it is possible for the appliance 20c to be adapted for use on the labial side of a patient's tooth, and include tiewings as desired. Moreover, the archwire slot 32c as illustrated in the drawings is open in an occlusal direction for entry of an archwire when the archwire is moved in a gingival direction, although it is also possible for the archwire slot to open in a horizontal direction for admitting an archwire when moved in a buccolabial direction (when the appliance is adapted for bonding to a lingual tooth surface) or in a lingual direction (when the appliance is adapted for bonding to a buccolabial tooth surface).

Figure 13:
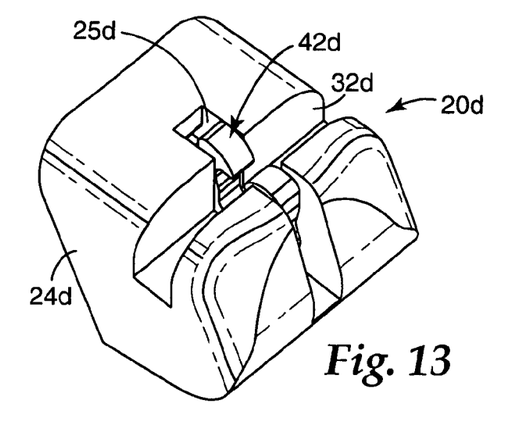
FIG. 13 is a perspective view of an orthodontic appliance according to still another embodiment of the invention, looking at the appliance in a direction toward its mesial, occlusal and lingual sides.
Figures 14, 15:
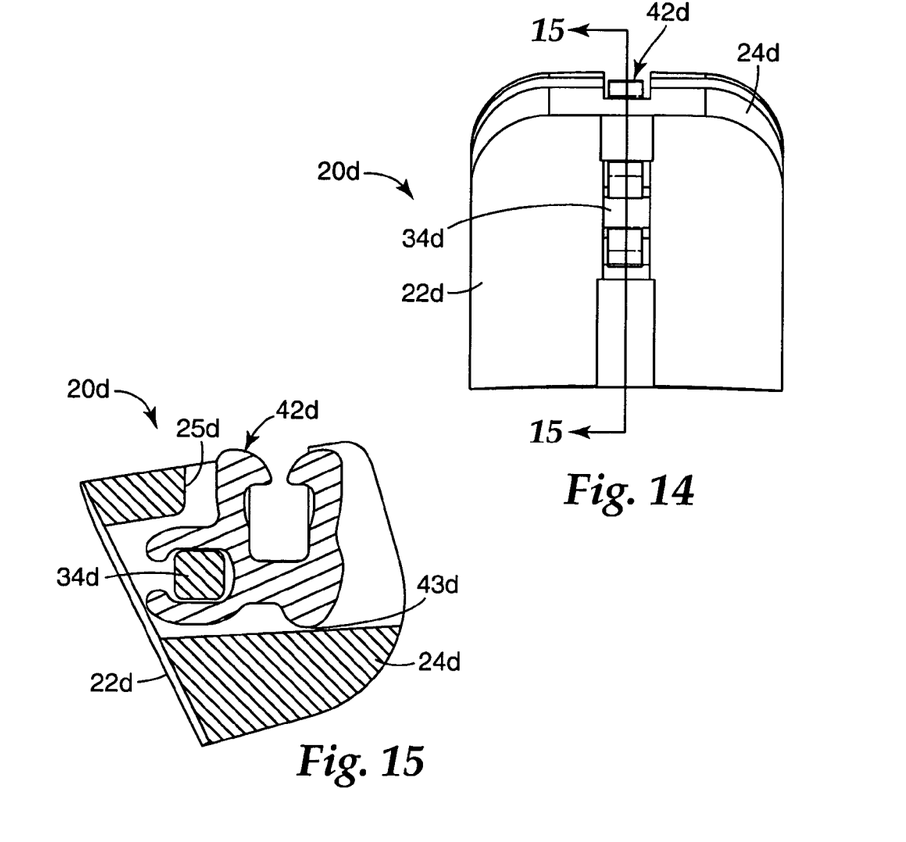
FIG. 14 is a rear elevational view of the appliance shown in FIG. 13, looking at the appliance in a direction toward its buccolabial side.
FIG. 15 is a side cross-sectional view of the appliance shown in FIGS. 13–14, taken along lines 15—15 of FIG. 14 and looking in a direction along a mesial-distal reference axis.

An orthodontic appliance 20d according to yet another embodiment of the invention is shown in FIGS. 13–15. The appliance 20d includes a base 22d for connection to a patient's tooth surface, along with a body 24d that extends outwardly from the base 22d. Except as described below, the appliance 20d is similar to the appliance 20c.

The appliance 20d includes a clip 42d that is received in a central cavity 25d of the body 24d. A post 34d, shown in FIGS. 14 and 15, extends across the cavity 25d in a generally mesial-distal direction, and preferably in a direction parallel to or at least generally parallel to the longitudinal axis of an archwire slot 32d. The post 34d preferably has a cross-sectional configuration that includes flat opposed sides, such as the rectangular configuration illustrated in FIG. 15.

The clip 42d is essentially identical to the clip 42c, except that the clip 42d includes a protrusion 43d that is located near the intersection of a first and third section of the clip 42d. The protrusion 43d, in combination with an adjacent inner wall of the body 24d defining the cavity 25d, serves to limit pivotal movement of the clip 42d in a clockwise direction viewing FIG. 15. The rectangular shape of the post 34d, in cooperation with adjacent flat edges of the clip 42d, also helps to limit pivotal movement of the clip 42d about the central axis of the post 34d.

The appliance 20d as shown in this embodiment of the invention lacks tiewings and is adapted for lingual use. However, the appliance 20d could be provided with tiewings and/or be adapted for buccolabial use if desired.

The invention described in the various embodiments above is advantageous in that the clips can be assembled to the posts after the posts have been connected to the appliance body by a brazing or welding process carried out at elevated temperatures. As a consequence, the clips need not be subjected to undue heat that might otherwise impair the resiliency of the clip material.

A number of other constructions are also possible. For example, the body of the appliances described above may be made of a metallic or plastic material. The invention is especially advantageous when the appliance includes a metallic base that is bonded to a metallic body by a process carried out at elevated temperatures such as a brazing process, since the clip(s) can be connected to the body after the elevated temperature processes have been completed.

Other variations are also possible. Accordingly, the invention should not be deemed limited to the specific examples that are set out above in detail, but instead only by a fair scope of the claims that follow along with their equivalents.

The invention claimed is:

1. An orthodontic appliance comprising:
a base;
a body extending outwardly from the base;
an archwire slot extending across the appliance in a generally mesial-distal direction, the archwire slot including an open side;
a post; and
a latch for releasably retaining an archwire in the archwire slot, wherein the latch includes a clip having a region with an opening adjacent the open side of the archwire slot for receiving an archwire, wherein the clip also includes a recess that receives the post, wherein the recess is not in communication with the archwire-receiving region, and wherein the clip is retained on the post when an archwire is admitted through the opening and into the archwire slot.

2. An orthodontic appliance according to claim 1 wherein the clip includes a leg section extending next to the recess, and wherein the leg section is movable in a direction away from the recess in order to admit the post into the recess.

3. An orthodontic appliance according to claim 2 wherein the leg section is made of a resilient material.

4. An orthodontic appliance according to claim 1 wherein the clip has a first section, a second section and a third section interconnecting the first section and the second section, and wherein the first section, the second section and the third section together present a generally "U"-shaped configuration and at least partially define the archwire-receiving region.

5. An orthodontic appliance according to claim 4 wherein the clip has a fourth section connected to the third section and a leg section connected to the fourth section, wherein the leg section and the third section extend in generally parallel directions.

6. An orthodontic appliance according to claim 5 wherein the leg section, the third section and the fourth section at least partially surround the recess.

7. An orthodontic appliance according to claim 5 wherein the clip has a pair of leg sections extending on opposite sides of the recess, and wherein each leg section is connected to the third section.

8. An orthodontic appliance according to claim 7 wherein the leg sections extend in directions generally parallel to each other.

9. An orthodontic appliance according to claim 8 wherein the first section and the second section extend in directions generally parallel to the direction of extension of the leg sections.

10. An orthodontic appliance according to claim 1 wherein the recess has an opening that is oriented to receive the post when the clip is moved in a direction generally along an occlusal-gingival reference axis relative to the post.

11. An orthodontic appliance according to claim 1 wherein the recess has an opening that is oriented to receive the post when the clip is moved in a direction along a generally buccolabial-lingual reference axis relative to the post.

12. An orthodontic appliance according to claim 1 wherein the appliance includes a second post, and wherein the clip includes a second recess that receives the second post.

13. An orthodontic appliance comprising:
a base;
a body extending outwardly from the base;
an archwire slot extending across the appliance in a generally mesial-distal direction;
a post; and
a latch for releasably retaining an archwire in the archwire slot, wherein the latch includes a clip having a region next to the archwire slot for receiving an archwire, wherein the clip also includes a recess that receives the post, and wherein the recess is not in communication with the archwire-receiving region,
wherein the appliance includes a second post, wherein the clip includes a second recess that receives the second post, wherein the clip includes a first section that extends next to an occlusal side of the archwire slot and the clip includes a second section that extends along a gingival side of the archwire slot, and wherein each of the first section and the second section extends along a respective one of the recesses.

14. An orthodontic appliance according to claim 1 wherein the post is connected to the body.

15. An orthodontic appliance according to claim 14 wherein the post extends in a direction generally along a mesial-distal reference axis.

16. An orthodontic appliance according to claim 14 wherein the body has a mesial and a distal side, and wherein the post extends in a direction generally perpendicular to at least one side.

17. An orthodontic appliance according to claim 1 wherein the post includes an enlarged head that extends past the recess.

18. An orthodontic appliance according to claim 1 wherein the latch includes a second clip.

19. An orthodontic appliance comprising:
a base;
a body extending outwardly from the base;
an archwire slot extending across the appliance in a generally mesial-distal direction;
a post; and
a latch for releasably retaining an archwire in the archwire slot, wherein the latch includes a clip having a region next to the archwire slot for receiving an archwire, wherein the clip also includes a recess that receives the post, and wherein the recess is not in communication with the archwire-receiving region, wherein the latch includes a second clip, wherein the body has a mesial side and a distal side, and wherein each of the sides is adjacent a respective one of the clips.

20. An orthodontic appliance comprising:
a base;
a body extending outwardly from the base;
an archwire slot extending across the appliance in a generally mesial-distal direction;
a post; and
a latch for releasably retaining an archwire in the archwire slot, wherein the latch includes a clip having a region next to the archwire slot for receiving an archwire, wherein the clip also includes a recess that receives the post, and wherein the recess is not in communication with the archwire-receiving region,
wherein the body includes a mesial section, a distal section and a cavity between the mesial section and the distal section, wherein the post extends in a cavity, and wherein the clip is received at least partially in the cavity.

21. An orthodontic appliance according to claim 20 wherein the archwire slot has a longitudinal axis, and wherein the post extends in a direction generally parallel to the longitudinal axis of the archwire slot.

22. An orthodontic appliance according to claim 1 wherein the post has at least one flat side, and wherein the clip includes at least one flat region in contact with the at least one flat side of a post.

23. An orthodontic appliance according to claim 1 wherein the clip includes at least two leg sections that extend in directions generally parallel to each other.

24. An orthodontic appliance according to claim 23 wherein the clip has a first section, a second section and a third section interconnecting the first section and the second section, and wherein the first section, the second section and the third section together present a generally "U"-shaped configuration and at least partially define the archwire-receiving region.

25. An orthodontic appliance according to claim 24 wherein at least two leg sections extend outwardly from the first section in directions generally along an occlusal-gingival reference axis.

26. An orthodontic appliance according to claim 25 wherein the clip includes two leg sections that extend outwardly from the first section in an occlusal direction, and two leg sections that extend outwardly from the second section in a generally gingival direction.

27. An orthodontic appliance according to claim 24 wherein at least two leg sections extend away from the third section in directions generally along a buccolabial-lingual reference axis.

28. An orthodontic appliance comprising:
a base;
a body extending outwardly from the base;
an archwire slot extending across the appliance in a generally mesial-distal direction;
a post; and
a latch for releasably retaining an archwire in the archwire slot, wherein the latch includes a clip having a region next to the archwire slot for receiving an archwire, wherein the clip also includes a recess that receives the post, and wherein the recess is not in communication with the archwire-receiving region,
wherein the appliance includes a second post, and wherein the clip also includes a second recess that receives the second post, and wherein the second recess is not in communication with the archwire-receiving region.

29. An orthodontic appliance according to claim 1 wherein the appliance farther includes an archwire slot liner defining the archwire slot, and wherein the archwire slot liner includes at least one end portion that extends beyond the body.

30. An orthodontic appliance comprising:
a base;
a body extending outwardly from the base;
an archwire slot extending across the appliance in a generally mesial-distal direction;
a post; and
a latch for releasably retaining an archwire in the archwire slot, wherein the latch includes a clip having a region next to the archwire slot for receiving an archwire, wherein the clip also includes a recess that receives the post, and wherein the recess is not in communication with the archwire-receiving region,
wherein the appliance further includes an archwire slot liner defining the archwire slot, and wherein the archwire slot liner includes at least one end portion that extends beyond the body, and wherein the end portion of the archwire slot liner extends across a portion of the clip.

31. An orthodontic appliance according to claim 30 wherein the end portion of the archwire slot liner extends in a direction generally along a buccolabial-lingual reference axis.

32. An orthodontic appliance according to claim 1 wherein the recess and the region each have openings that are oriented at angles of approximately 90 degrees relative to each other.

33. An orthodontic appliance according to claim 1 wherein the recess and the region each have openings that are oriented at angles of approximately 180 degrees relative to each other.

* * * * *

UNITED STATES PATENT AND TRADEMARK OFFICE
CERTIFICATE OF CORRECTION

PATENT NO. : 7,140,876 B2 Page 1 of 1
APPLICATION NO. : 10/698285
DATED : November 28, 2006
INVENTOR(S) : David K. Cinader, Jr.

It is certified that error appears in the above-identified patent and that said Letters Patent is hereby corrected as shown below:

Title page item (75), Inventors: after "Cinader", insert --Jr.-- .

Column 9
Line 28, Delete "61 a" and insert --61a-- therefore.

Column 16
In Claim 29, delete "farther" and insert --further-- therefore.

Signed and Sealed this

Sixth Day of March, 2007

JON W. DUDAS
*Director of the United States Patent and Trademark Office*